(12) United States Patent
Panz

(10) Patent No.: US 6,550,933 B1
(45) Date of Patent: Apr. 22, 2003

(54) ARRAY AND METHOD FOR ILLUMINATING THE SKIN SURFACE OF AN EXAMINED PERSON

(76) Inventor: Ulla-Monika Panz, Hauptstrasse 57, D-71566 Althütte (DE)

(*) Notice: Subject to any disclaimer, the term of this patent is extended or adjusted under 35 U.S.C. 154(b) by 0 days.

(21) Appl. No.: 09/787,790
(22) PCT Filed: Sep. 18, 1999
(86) PCT No.: PCT/EP99/06927
§ 371 (c)(1), (2), (4) Date: Jun. 28, 2001
(87) PCT Pub. No.: WO00/18296
PCT Pub. Date: Apr. 6, 2000

(30) Foreign Application Priority Data
Sep. 25, 1998 (DE) .......... 198 44 045

(51) Int. Cl.⁷ .............. F21V 9/00; F21S 4/00
(52) U.S. Cl. .......... 362/231; 362/572; 600/306
(58) Field of Search .......... 362/231, 33, 804, 362/12, 140, 572; 600/249, 306, 309, 310, 476, 478; 606/3, 18, 12

(56) References Cited

U.S. PATENT DOCUMENTS 4,752,863 A * 6/1988 Parrott .......... 362/128
4,844,069 A * 7/1989 Mori .......... 128/396

FOREIGN PATENT DOCUMENTS

| CA | WO 98/46133 | * 10/1998 |
| DK | WO 91/14159 | * 9/1991 |

* cited by examiner

Primary Examiner—Stephen Husar
Assistant Examiner—Bao Truong
(74) Attorney, Agent, or Firm—Pendorf & Cutliff

(57) ABSTRACT

The invention relates to an array and a method for illuminating a skin surface of an examined person, especially the face, with the purpose of examining and determining the effect of color on the skin surface. Several light sources having different colors are provided for illumination. The intensity of said light sources can be adjusted individually.

16 Claims, 1 Drawing Sheet

ARRAY AND METHOD FOR ILLUMINATING THE SKIN SURFACE OF AN EXAMINED PERSON

BACKGROUND OF THE INVENTION

Field of the Invention

The invention concerns an array and a method for illuminating the skin surface of a subject, especially the area of the face, for the purpose of examining and determining the effect of color on the skin surface.

Research has shown that different individuals exhibit different emissions in response to illumination with various colors of light, this being due to differences pigmentation, hair coloring, eye coloring and facial shape. Depending upon the color composition of the light illuminating the subject there is produced thereby a facial impression which can be considered to be more positive or more negative.

SUMMARY OF THE INVENTION

The task of the invention is thus to produce a reproducible environment in which it is possible to illuminate the face of a subject with variously colored light in a defined manner.

The invention is based principally upon on recognition that a reliable determination of the skin-surface based color effect can only be achieved when a defined illumination environment is established. Thus, according to the invention, multiple light sources of varying color are provided for illumination, of which the intensity is individually adjustable. Preferably light sources for the colors red, yellow, green and blue are provided, wherein however multiple light sources of the same color could be provided, and wherein the light sources for each color group could preferably be adjusted as one unit with respect to their intensity.

Light sources can be adjusted or positioned in particularly simple manner when they are provided upon at least one carrier rail. Preferably, the light sources are however provided on at least two parallel carrier rails provided spaced apart from each other. This has been found to be particularly useful, because in this manner the various colored light sources can be positioned in defined separation from the person being examined, and allow themselves to be used to produce a defined illumination effect. In order to avoid the adverse effect upon the evaluation by foreign light, and in order to avoid the possible blocking of the radiated light between the light source and the person being examined, the light sources are preferably provided on the ceiling of a darkenable room. A particularly preferred illumination situation is produced when the blue and green light sources are provided on a first mounting rail and the red and yellow light sources are provided on a second mounting rail. A subjective even illumination distribution is produced when on the first mounting rail three blue and two green light sources are provided in the sequence blue-green-blue-green-blue and upon the second mounting rail a yellow and two red light sources are provided in the sequence red-yellow-red. Therein the mounting rails with the blue and green light sources should be positioned closer to the person being examined than the mounting rails with the yellow and red light sources.

It has been found to be advantageous, when the subject being examined is included in the evaluation process. Thus a mirror should be provided in the illumination path between the light sources and the subject. The subject is herein positioned in front of the mirror and is illuminated by reflection off of the mirror. In this manner both the person providing the advice and the subject can simultaneously observe and evaluate the effect of the illumination with different colors. A defined and reproducible illumination situation results when the light sources are so oriented, that the maximal intensity of their illumination field is directed upon the subject being examined. Thereby the light sources are preferably designed as reflection emitters or triangular emitters.

In order to produce comparable results with respect to the color effect in spaces of different sizes, the relationship of the room height to the distance of the mounting rails or as the case may be light sources from the mirror should be approximately 4:3:2 and the relationship of the distance of the chair and the mounting rails from the mirror should be approximately 3:5:7. The room height is preferably selected as the reference size, so that for different room heights the distance of the mounting rails or as the case may be light sources from the mirror can be appropriately adapted or adjusted.

For changing the illumination intensity the light sources or light source groups are preferably adjustable in their intensity or brightness via an installed adjustment element. The adjustment element can for example be a dimmer, which is provided with a scale ranging from 0% to 100%. For illumination of the darkened room prior to or after the consultation, at least one supplemental white light source should be provided which is adjustable with respect to its intensity.

The examination and judging of a color effect upon a skin surface is inventively carried out in such a manner, that for illumination multiple light colors are employed individually and/or in combinations, wherein at least one part of the light color or spectrum is varied with respect to its brightness contribution. Preferably, in accordance with a first process step there occurs illumination sequentially with respectively one of the light colors with defined reference intensity, and in a second process step one of the light colors is selected for reference intensity and at least one further light color is mixed in with differing illumination contributions.

BRIEF DESCRIPTION OF THE DRAWING

In the following the invention will be described in greater detail on the basis of the arrangement schematically shown in the drawing. There is shown FIG. 1 a side view of an inventive arrangement; and FIG. 2 a view from above upon the arrangement according to

DETAILED DESCRIPTION OF THE INVENTION

Figure 1:
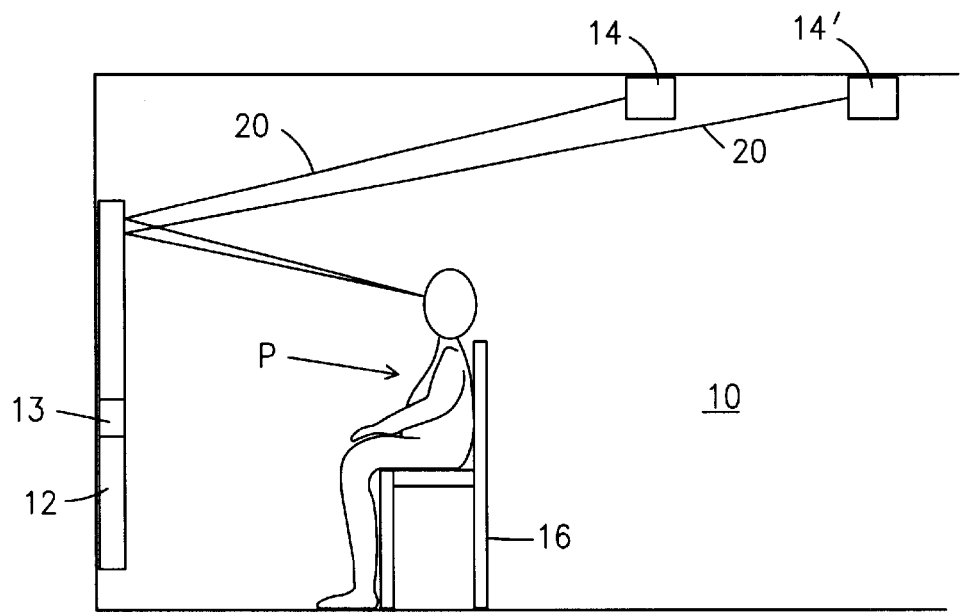
Figure 2:
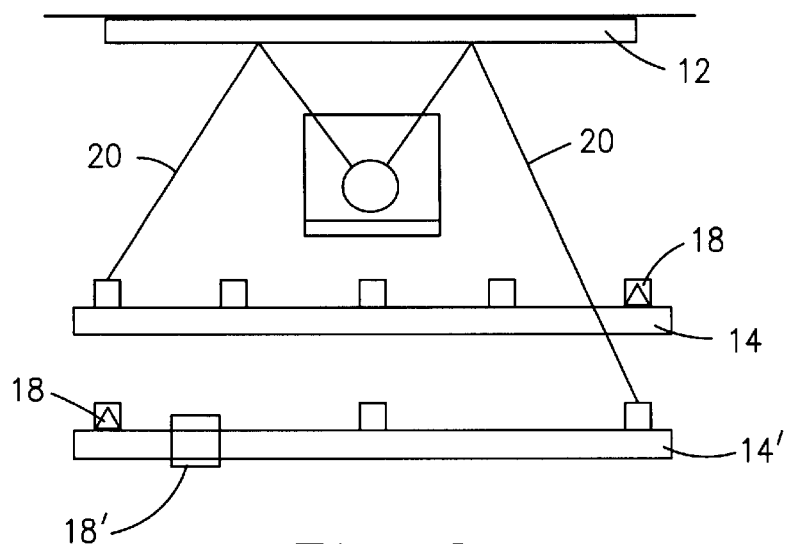

The figure shows schematically a room which can be darkened 10, in which a mirror 12 is provided on one wall and two mounting rails 14, 14' are provided on the ceiling thereof. In front of the mirror 12 a chair 16 is provided in such a manner that a subject P seated thereon faces the mirror and can observe himself in the mirror. On each of the mounting rails 14 there is a row of light sources 18, wherein on the mounting rail closer to the subject P five light sources are provided and on the other mounting rail three light sources are provided (FIG. 2). The light sources 18 are triangular emitters, of which the maximum illumination is directed, via the mirror 12, upon the face of the subject P, as shown by lines 20. For illumination of the darkened room prior to or after the consultation a supplemental white light source 18' is provided and is adjustable with respect to its intensity.

The light sources 18 exhibit the colors blue, green, yellow and red, wherein on the mounting rail 14 three blue -and two green light sources are provided in the sequence blue-green-blue-green-blue and on the mounting rail 14' two red light sources and one yellow light source are provided in the sequence red-yellow-red. For changing of the illumination intensity of a color, all light sources 18 of the same color are controlled as one unit by means of an adjustment element which is in the form of a scaled adjusted element 13.

In order to produce comparable results with respect to the color effect even in rooms of different sizes, the relationship of the room height to the distance of the mounting rails 14, 14' or the light sources 18 from the mirror 12 correspond to approximately 4:3:2 and the relationship of the distance of the chair 16 and the mounting rails 14, 14' from the mirror 12 correspond to approximately 3:5:7. As reference value, the room height is preferably selected, so that in rooms of different height the distance of the mounting rails 14, 14' or as the case may be the light sources 18 from the mirror 12 are appropriately adjusted or adapted.

EXAMPLE

A mirror of 180 cm height and 150 cm width is secured to the wall of a 260 cm high room 10 spaced 20 cm above the floor. On the ceiling of the room the mounting rails 14, 14' are provided with distances of 140 cm and 200 cm from the mirror 12. The chair 16 is placed in front of the mirror 12 in such a manner that the face of the subject P is positioned at a height of approximately 110 cm and with a distance of 90 cm from the mirror.

For determining the color effect, the subject takes a seat upon the chair 16 and the room 10 is darkened. First a base color is determined which fits the subject, that is, produces a positive impression, wherein the subject P is sequentially illuminated with each of the four available colors with maximum intensity. Thereafter, in certain cases after reduction of the intensity of the base color, the further colors are iteratively mixed in, with variations of the their intensity. As a general rule the mixture of two colors produces an optimal result; it could however be possible to use three or even all four colors in order to produce an optimal result.

In the case of a first subject using the above method a color mixture of 40% yellow and 60% blue, respectively based upon their maximal intensity, was determined to be the ideal color mixture while in a second subject a mixture of 80% yellow and 20% red was found to be ideal.

In summary the following was concluded: The invention concerns a device as well as a process for illumination of the skin surface of a subject, in particular in the area of the face, for the purpose of examining and judging the color effect upon the skin surface. Multiple light sources of different color are provided for producing this illumination, of which the intensity is individually adjustable.

What is claimed is:

1. A device for illumination of skin surface of subject for the purpose of examining and judging the color effect produced by the skin surface, said a device comprising:

at least first and second light sources for emitting colored light, said second light source emitting a color different from said first light source color, said light sources adjustable in intensity wherein multiple groups of light sources of different color are provided, and wherein the light sources of each of the respective color groups are adjustable as a unit with respect to their intensity.

2. A device as in claim 1, comprising light sources of at least three different colors.

3. A device according to claim 2, comprising red, yellow, green and blue light sources.

4. A device according to claim 3, wherein the blue and green light sources are provided on a first mounting rail and the red and yellow light sources are provided upon a second mounting rail.

5. A device according to claim 4, wherein three blue and two green light sources are provided on the first mounting rail in the sequence blue-green-blue-green-blue, and wherein a yellow and two red light sources are provided the second mounting rail in the sequence red-yellow-red.

6. A device according to claim 4, wherein the mounting rail with the blue and green light sources is provided closer to the subject than the mounting rail with the yellow and red light sources.

7. A device according to claim 1, wherein a mirror is provided in the illumination path between the light sources and the subject.

8. A device according to claim 1, wherein the light sources are so oriented that the maximal intensity of their illumination field is directed upon the surface of skin being examined.

9. A device according to claim 1, wherein the light sources are triangular emitters.

10. A device according to claim 1, wherein the light sources or light source groups are adjustable in their intensity via respectively a scaled adjusted element.

11. A device for illumination of skin surface of subject for the purpose of examining and judging the color effect produced by the skin surface, said a device comprising:

at least first and second light sources for emitting colored light, said second light source emitting a color different from said first light source color, said light sources adjustable in intensity wherein the light sources are provided upon at least one mounting rail.

12. A device according to claim 11, wherein the light sources are provided upon two mounting rails, said rails provided spaced apart from each other and parallel to each other.

13. A device for illumination of skin surface of subject for the purpose of examining and judging the color effect produced by the skin surface, said a device comprising:

at least first and second light sources for emitting colored light, said second light source emitting a color different from said first light source color, said light sources adjustable in intensity wherein the light sources are provided on the ceiling of a room which can be darkened.

14. A device for illumination of skin surface of subject for the purpose of examining and judging the color effect produced by the skin surface, said a device comprising:

at least first and second light sources for emitting colored light, said second light source emitting a color different from said first light source color, said light sources adjustable in intensity at least one supplemental white light source, wherein the intensity of the supplemental light source can be adjustable.

15. A process for illumination of the surface of the skin of a subject for the purpose of examining and determining the color response characteristic of the skin surface, comprising:
   (a) providing at least first and second light emitters for emitting light of different colors,
   (b) illuminating said skin surface with one or more of said light emitters at a fixed intensity, and
   (c) illuminating said skin surface with one or more light sources to bring about a change in the balance of colors illuminating said skin surface
   wherein the light sources are adjustable in their intensity via a scaled adjusted element.

16. A process for illumination of the surface of the skin of a subject for the purpose of examining and determining the color response characteristic of the skin surface, comprising:
   (a) providing at least first and second light emitters for emitting light of different colors,
   (b) illuminating said skin surface sequentially with respectively one of the light colors with defined illumination intensity, and
   (b) illuminating said skin surface with one or more of said light emitters at a fixed reference intensity while illuminating said skin surface with one or more light sources to bring about a change in the balance of colors illuminating said skin surface
   wherein the light sources are adjustable in their intensity via a scaled dimmer.

* * * * *